United States Patent
Yang et al.

(10) Patent No.: US 10,409,639 B2
(45) Date of Patent: Sep. 10, 2019

(54) TASK SCHEDULING SYSTEM WITH A WORK BREAKDOWN STRUCTURE AND METHOD SUITABLE FOR MOBILE HEALTH

(71) Applicant: Hefei University of Technology, Hefei (CN)

(72) Inventors: Shanlin Yang, Hefei (CN); Shuai Ding, Hefei (CN); Wenjuan Fan, Hefei (CN); Hao Wang, Hefei (CN); Jinxin Pan, Hefei (CN); Shikang Hu, Hefei (CN); Hui Huang, Hefei (CN)

(73) Assignee: Hefei University of Technology, Hefei (CN)

( * ) Notice: Subject to any disclaimer, the term of this patent is extended or adjusted under 35 U.S.C. 154(b) by 29 days.

(21) Appl. No.: 15/809,993

(22) Filed: Nov. 10, 2017

(65) Prior Publication Data
US 2018/0136974 A1 May 17, 2018

(30) Foreign Application Priority Data
Nov. 15, 2016 (CN) .......................... 2016 1 1004901

(51) Int. Cl.
G06F 9/48 (2006.01)
G06F 19/00 (2018.01)
G16H 40/20 (2018.01)

(52) U.S. Cl.
CPC .......... *G06F 9/4881* (2013.01); *G06F 19/325* (2013.01); *G06F 19/3418* (2013.01); *G16H 40/20* (2018.01)

(58) Field of Classification Search
None
See application file for complete search history.

(56) References Cited

U.S. PATENT DOCUMENTS

2006/0293939 A1* 12/2006 Sun .................. G06Q 10/06
 705/7.14
2015/0081912 A1* 3/2015 Tan .................. H04L 67/1038
 709/226

FOREIGN PATENT DOCUMENTS

| CN | 103279385 A | 9/2013 |
| CN | 104636202 A | 5/2015 |
| CN | 105260232 A | 1/2016 |
| CN | 105893157 A | 8/2016 |
| EP | 2977898 A1 | 1/2016 |

* cited by examiner

*Primary Examiner* — Meng Ai T An
*Assistant Examiner* — Zujia Xu
(74) *Attorney, Agent, or Firm* — Wayne & Ken, LLC; Tony Hom

(57) ABSTRACT

The present invention discloses a task scheduling system and method suitable for mobile health, the characteristics thereof including: a mobile health task distribution module, a plurality of mobile health task processing modules and a mobile health task callback module; the mobile health task distribution module comprises: a resource description unit, a resource scheduling unit, a resource matcher; each of the mobile health task processing modules comprises: a task decomposition unit, a task execution unit, a task evaluation unit. The present invention is capable of carrying out tasks with full use of the currently available task processing resources, thereby being capable of improving the efficiency and performance of the task scheduling processing in the mobile health environment.

1 Claim, 2 Drawing Sheets

TASK SCHEDULING SYSTEM WITH A WORK BREAKDOWN STRUCTURE AND METHOD SUITABLE FOR MOBILE HEALTH

TECHNICAL FIELD

The present invention relates to the technical field of mobile health, and specifically, to a task scheduling system and method suitable for mobile health.

BACKGROUND

The process of task scheduling is a type of application issue with strong background. However, health tasks have a very high requirement for the processing of sensitive information and the task timeliness due to their particular industry background. With the growing popularity of mobile internet, an increasing number of users begin to use different mobile devices for treatment, inquiry, and medical meetings etc. through the internet. In order to normally process this series of mobile health tasks, there is a need for combining the features of tasks to conduct corresponding mobile health resource scheduling, thereby guaranteeing that the mobile health tasks generated by the interactions between doctors and patients, and between doctors can be processed very well. However, the existing task scheduling methods have the following defects:

1. There is an "unclassified" problem in the task scheduling of the existing methods applied to mobile health environment, that is, health tasks of different types such as the non-real-time information exchange between doctors and patients, and the real-time links during diagnosis and treatment etc. are not effectively classified, thereby leading to an uneven and inefficient distribution of the facility resources that support mobile health services.

2. The existing task scheduling methods do not concern the process of mobile health tasks, but only focus on their process results. Such process methods cannot achieve real-time monitoring of the resources during the mobile health services, therefore quantities of abnormal interruptions, waste of resources and other issues may occur, affecting the quality of mobile health services.

SUMMARY

In order to overcome the shortcomings that exist in the prior art, the present invention provides a task scheduling system and method suitable for mobile health, expecting to fully and evenly utilize the processing resources to be allocated for mobile health tasks, and select the optimal resources in the case of abundant resources, thereby improving the efficiency of utilizing the mobile health resources and the quality of tasks processing.

In order to realize the above-mentioned objectives of the present invention, the following technical solutions are employed:

A task scheduling system suitable for mobile health of the present invention is characterized in that it comprises: a mobile health task distribution module, n mobile health task processing modules and a mobile health task callback module.

The mobile health task distribution module comprises: a resource description unit, a resource scheduling unit, a resource matcher.

Each of the mobile health task processing modules comprises: a task decomposition unit, a task execution unit, a task evaluation unit.

The resource description unit receives the health tasks sent externally and utilizes an Resource Description and Access (RDA) framework for description and classification, so as to obtain mobile diagnosis and treatment tasks and intelligent health tasks; then measures the mobile diagnosis and treatment tasks and intelligent health tasks, packages the mobile diagnosis and treatment tasks and intelligent health tasks respectively after obtaining the corresponding resource descriptors, so as to obtain the mobile diagnosis and treatment tasks with the resource descriptors and intelligent health tasks with the resource descriptors.

The resource scheduling unit identifies task priorities for the mobile diagnosis and treatment tasks with the resource descriptors and the intelligent health tasks with the resource descriptors respectively with a secondary scheduling method, so as to obtain a resource schedule table.

The resource matcher matches corresponding optimal resources for the mobile diagnosis and treatment tasks with the resource descriptors and the intelligent health tasks with the resource descriptors by annealing algorithm; and sends the mobile diagnosis and treatment tasks with the resource descriptors and the intelligent health tasks with the resource descriptors to the mobile health task processing module corresponding to the optimal resources.

The task decomposition unit in the corresponding health task processing module describes the smallest granularity tasks that can be handled by itself with a work decomposition structure dictionary, and obtains an Work Breakdown Structure (WBS); thereby utilizing the WBS to match the received mobile diagnosis and treatment tasks with the resource descriptors and the intelligent health tasks with the resource descriptors, if matches successfully, it indicates that the received mobile diagnosis and treatment tasks with the resource descriptors and the intelligent health tasks with the resource descriptors are indecomposable, otherwise they are regarded as decomposable; and decomposes the mobile diagnosis and treatment tasks with the resource descriptors and the intelligent health tasks with the resource descriptors that are decomposable according to the WBS, so as to obtain the mobile diagnosis and treatment tasks with the resource descriptors and the intelligent health tasks with the resource descriptors that have the smallest granularity.

The task execution unit processes the mobile diagnosis and treatment tasks and the intelligent health tasks processed by the task decomposition unit respectively and accordingly with the optimal resources, thereby obtaining the process results of the intelligent health tasks; and makes dynamic evaluations with the task evaluation unit during the processing of the mobile diagnosis and treatment tasks, so as to obtain the process results of the mobile diagnosis and treatment tasks.

The health task callback module judges the process results of the intelligent health tasks and the mobile diagnosis and treatment tasks, if the process results are successful, notifies the corresponding health task processing module to release the matched optimal resources; otherwise, generates and sends an error code to the resources matcher of the health task distribution module to rematch resources.

A task scheduling method suitable for mobile health of the present invention is characterized in that it is performed according to the following steps:

step 1. describing and classifying health tasks with a RDA framework, so as to obtain mobile diagnosis and treatment tasks and intelligent health tasks;

step 2. measuring the mobile diagnosis and treatment tasks and intelligent health tasks, packaging the mobile diagnosis and treatment tasks and intelligent health tasks respectively after obtaining the corresponding resource descriptors, so as to obtain the mobile diagnosis and treatment tasks with the resource descriptors and intelligent health tasks with the resource descriptors;

step 3. identifying task priorities for the mobile diagnosis and treatment tasks with the resource descriptors and the intelligent health tasks with the resource descriptors respectively with a secondary scheduling method, so as to obtain a resource schedule table;

step 4. matching the corresponding optimal resources for the mobile diagnosis and treatment tasks with the resource descriptors and the intelligent health tasks with the resource descriptors with annealing algorithm;

step 5. matching the mobile diagnosis and treatment tasks with the resource descriptors and the intelligent health tasks with the resource descriptors with WBS decomposition structure, if matching successfully, it indicates that the received mobile diagnosis and treatment tasks with the resource descriptors and the intelligent health tasks with the resource descriptors are indecomposable, otherwise they are regarded as decomposable;

step 6. decomposing the mobile diagnosis and treatment tasks with the resource descriptors and the intelligent health tasks with the resource descriptors that are decomposable according to the WBS, so as to obtain the mobile diagnosis and treatment tasks with the resource descriptors and the intelligent health tasks with the resource descriptors that have the smallest granularity;

step 7. processing the mobile diagnosis and treatment tasks and the intelligent health tasks processed by the task decomposition unit respectively and accordingly with the optimal resources, thereby obtaining the process results of the intelligent health tasks; and making dynamic evaluations during the processing of the mobile diagnosis and treatment tasks, thereby obtaining the process results of the mobile diagnosis and treatment tasks;

step 8. judging the process results of the intelligent health tasks and the mobile diagnosis and treatment tasks, if the process results are successful, releasing the matched optimal resources; otherwise, returning to the step 4 to rematch resources.

Compared with the prior art, the advantages of the present invention lie in that:

1. for the task scheduling system and method suitable for mobile health established by the present invention, the task processing environment is located on a remote server, the initiator of a task could be any terminal device that is linked to the server, the system improves the resources utilization efficiency by decomposing and matching the optimal resources according to the task type, and evaluating the quality of the resources according to the task execution status, and adjusting the resource distributions depending on the quality.

2. for the task scheduling system and method suitable for mobile health established by the present invention, the task scheduling method thereof is not limited by the specific task type, it employs an unification-first-then-classification way for the task processing procedure, so that the platform can achieve expansion without modifying the system when new types of task are generated during application.

3. for the task scheduling system and method suitable for mobile health established by the present invention, the mobile health task distribution module thereof utilizes the RDA framework to describe health tasks sent externally, and may classify any of the current tasks according to this general framework description method, thereby preprocessing the tasks without affecting the process efficiency before processing the tasks and improving the process efficiency of subsequent steps.

4. for the task scheduling system and method suitable for mobile health established by the present invention, the resource matcher in the mobile health task distribution module thereof will use an improved annealing algorithm, and take the process results of all the resources as a parameter of annealing time in the annealing algorithm, thereby improving the annealing convergence speed when an error occurs during the processing, which increases the process efficiency.

5. for the task scheduling system and method suitable for mobile health established by the present invention, the task decomposition unit in the mobile health task processing module thereof uses the WBS decomposition structure to perform a granularity match on tasks, and the description method the WBS decomposition structure utilizes to divide the tasks from top to bottom is of tree structure, thereby guaranteeing that the tasks do not depart from the WBS decomposition structure when divided, so that the decomposition of the tasks will not affect the normal completion of the tasks.

6. for the task scheduling system and method suitable for mobile health established by the present invention, the task evaluation unit in the mobile health task processing module thereof continues to evaluate the mobile diagnosis and treatment tasks, monitors the execution of the mobile diagnosis and treatment tasks in real time, and feeds it back into the mobile health task distribution module, thereby improving the probability of success when the mobile diagnosis and treatment tasks are executed and reducing the risk of failure.

DETAILED DESCRIPTION

Figure 1:
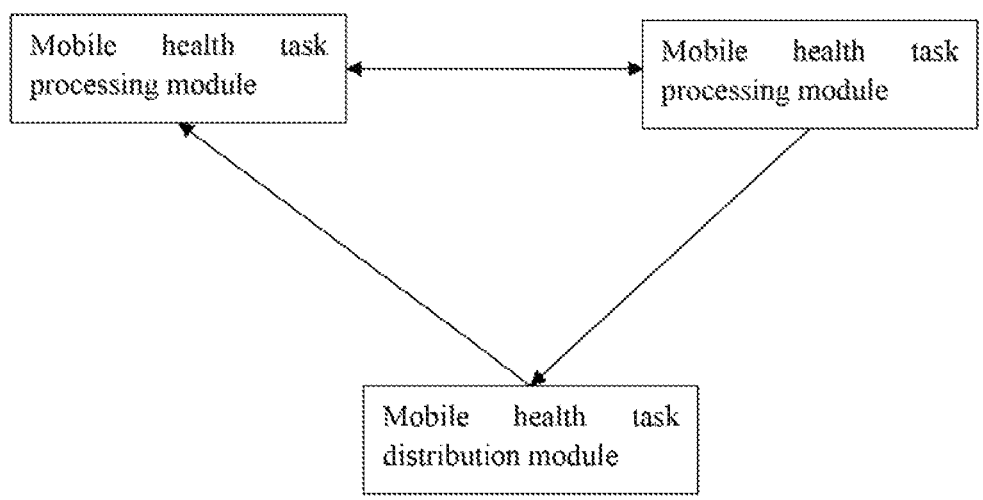
FIG. 1 is a basic structural diagram of the system of the present invention.
Figure 2:
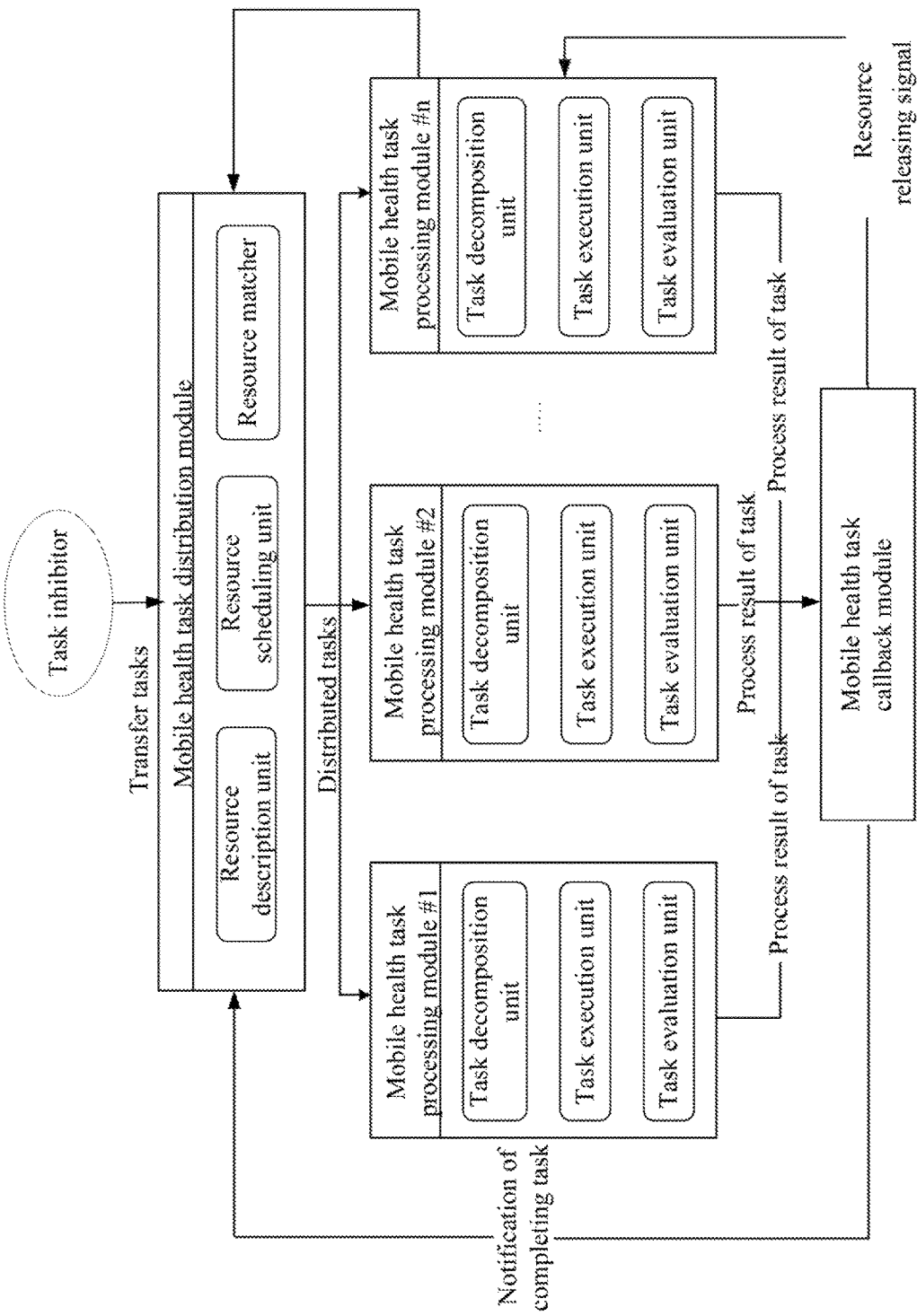
FIG. 2 is a flow chart of the method of the present invention.

In the present embodiment, a task scheduling system suitable for mobile health, as illustrated in FIGS. 1 and 2, comprises: a mobile health task distribution module, n mobile health task processing modules and a mobile health task callback module.

The mobile health task distribution module is a type of software that is supported by the server and the network infrastructure, it is mainly used to describe an externally initiated task after receiving it so as to obtain a classified task, so that the classified task can be placed in a scheduling queue, the optimal resources will process different tasks depending on the queue. The mobile health task distribution module comprises: a resource description unit, a resource scheduling unit, a resource matcher.

The mobile health task processing module is a software that is located in a different infrastructure from that of the mobile health tasks, it is composed of a plurality of server groups and firewall facilities, mainly used to decompose the tasks distributed by the mobile health task distribution module, and process the decomposed tasks meanwhile evaluates part of the tasks during the process. Each of the mobile health task processing modules comprises: a task decomposition unit, a task execution unit, a task evaluation unit.

Before receiving the external tasks, a set of Resource Description and Access (RDA) framework information has been preset in the current mobile health task distribution module, the resource description unit receives the health tasks sent externally and utilizes the RDA framework for description and classification, the specific way of description is: finding the health classification directory in the RDA master directory, judging the type of tasks according to two basic types defined subjectively under this classification directory to obtain mobile diagnosis and treatment tasks and intelligent health tasks; if the tasks do not belong to these two task types, classifying none of the tasks and removing them from the task scheduling system; then measuring the mobile diagnosis and treatment tasks and intelligent health tasks, the way of measuring is to take the size of the task files included in the intelligent health tasks to be processed as a primary indicator, and take the communication requirement of the mobile diagnosis and treatment tasks to be processed as a primary indicator, the primary indicators are all divided into 5 levels, each level from high to low corresponds to a different task measurement level respectively, and the primary indicators and the current timestamp together constitute the resource descriptors; after obtaining the corresponding resource descriptors, packaging them with the mobile diagnosis and treatment tasks and intelligent health tasks respectively, thus obtaining the mobile diagnosis and treatment tasks with the resource descriptors and intelligent health tasks with the resource descriptors.

Alter obtaining the corresponding tasks with the resource descriptors, the resource scheduling unit identifies task priorities for the mobile diagnosis and treatment tasks with the resource descriptors and the intelligent health tasks with the resource descriptors respectively with a secondary scheduling method, the secondary scheduling method will utilize the primary indicators of the resource descriptors as the reference indicators of the first scheduling, after obtaining a scheduling cache table, the secondary scheduling method takes the timestamp as an indicator of optimization and adjustment, and updates the schedule cache table, thereby obtaining a resource schedule table.

The resource schedule table will obtain a task queue to be processed, the resource matcher will allocate the resources needed for the tasks based on this resource schedule table, and the resource matcher matches corresponding optimal resources for the mobile diagnosis and treatment tasks with the resource descriptors and the intelligent health tasks with the resource descriptors with annealing algorithm; in the process of implementation, the annealing algorithm regards n mobile health task processing modules as a mesh structure, and further regards the time needs to be spent by tasks passing through this server as a part of the weight value of the path, the completion of earlier tasks in this path is the other part of the weight value of the path.

The annealing algorithm will perform the optimal selection according to the following steps:

step 1: selecting an initial resource processing module $X_0$ as the optimal resource, recording the current iteration step k=0 and the current temperature $t_k=t_{max}$;

step 2: proceeding to 3) if the cycle-stop condition is reached at this temperature. Otherwise, selecting a neighbor $x_j$ randomly from field $N(x_i)$, calculating and obtaining $\Delta fij=f(x_j)-f(x_i)$, if $\Delta f_{ij} \leq 0$, then $x_i=x_j$; otherwise if $\exp(-\Delta f_{ij}/t_k)>\text{random}(0,1)$, then $x_i=x_j$, repeating the step 2;

step 3 k=k+1, $t_{k+1}=d(t_k)$, wherein $d(t_k)$ indicates the function of temperature drop, if the condition is satisfied, proceeding to step 4, otherwise proceeding to the step 2;

step 4: calculating the results of the optimal resources, stopping; and step 5: sending the mobile diagnosis and treatment tasks with the resource descriptors and the intelligent health tasks with the resource descriptors to the mobile health task processing module corresponding to the optimal resources.

The task decomposition unit in the corresponding health task processing module describes the smallest granularity tasks that can be handled by itself with a work decomposition structure dictionary, the words in the decomposition dictionary are predefined by the system, the tasks are decomposed step-by-step from the root in a top-to-down order in the process of definition, and an Work Breakdown Structure (WBS) is obtained; thereby utilizing the WBS to match the received mobile diagnosis and treatment tasks with the resource descriptors and the intelligent health tasks with the resource descriptors, the success and failure of the match depends on whether the level that the tasks match reaches is a leaf node, if it is a leaf node, the match is regarded as successful, and if matches successfully, it indicates that the received mobile diagnosis and treatment tasks with the resource descriptors and the intelligent health tasks with the resource descriptors are indecomposable, otherwise they are regarded as decomposable; and decomposes the mobile diagnosis and treatment tasks with the resource descriptors and the intelligent health tasks with the resource descriptors that are decomposable according to the WBS, the form of decomposition depends on the task level in which the current task is, the tasks in high level necessarily can be decomposed down into tasks with smaller granularity through the WBS decomposition structure, the same resource descriptors are retained during the decomposition, and the mobile diagnosis and treatment tasks with the resource descriptors and the intelligent health tasks with the resource descriptors that have the smallest granularity will be obtained after dividing the tasks into the leaf nodes.

The task execution unit processes the mobile diagnosis and treatment tasks and the intelligent health tasks processed by the task decomposition unit respectively and accordingly with the optimal resources, thereby obtaining the process results of the intelligent health tasks; and makes dynamic evaluations with the task evaluation unit during the processing of the mobile diagnosis and treatment tasks, the results of the evaluations are determined based on a dynamically changing parameter Q, which will continuously change in the process of performing the tasks and is controlled by the following process:

1) in the process of performing the tasks, analyzing the R-Factor values by capturing data packets during the call in the network, the basic calculation formula is R=Ro−Is−Id−Ie+A, when R is less than 50, Q=Q−5;

2) for the tasks whose level is i in the primary indicators, in the case that the correct response is not obtained within a limited time (30 s), applying $Q_n=Q_p-(5-i)*10$, wherein $Q_p$ refers to the current value of Q, $Q_n$ refers to the value of Q in the next calculation node, continuously calculating the value of Q in this way, when Q is less than 50, the mobile diagnosis and treatment tasks are regarded as failed, otherwise successful, thereby obtaining the process results of the mobile diagnosis and treatment tasks.

The health task callback module judges the process results of the intelligent health tasks and the mobile diagnosis and treatment tasks, if the process results are successful, the module notifies the corresponding health task processing module to release the matched optimal resources; otherwise, generates and sends an error code to the resources matcher of the health task distribution module to rematch resources. The specific steps are as follows:

In the present embodiment, as illustrated in FIG. 2, a task scheduling method suitable for mobile health is performed according to the following steps:

step 1. describing and classifying health tasks with a RDA framework, so as to obtain mobile diagnosis and treatment tasks and intelligent health tasks;

step 2. measuring the mobile diagnosis and treatment tasks and intelligent health tasks, packaging the mobile diagnosis and treatment tasks and intelligent health tasks respectively after obtaining the corresponding resource descriptors, so as to obtain the mobile diagnosis and treatment tasks with the resource descriptors and intelligent health tasks with the resource descriptors;

step 3. identifying task priorities for the mobile diagnosis and treatment tasks with the resource descriptors and the intelligent health tasks with the resource descriptors respectively with a secondary scheduling method, so as to obtain a resource schedule table;

step 4. matching the corresponding optimal resources for the mobile diagnosis and treatment tasks with the resource descriptors and the intelligent health tasks with the resource descriptors with annealing algorithm;

step 5. matching the mobile diagnosis and treatment tasks with the resource descriptors and the intelligent health tasks with the resource descriptors with WBS decomposition structure, if matching successfully, it indicates that the received mobile diagnosis and treatment tasks with the resource descriptors and the intelligent health tasks with the resource descriptors are indecomposable, otherwise they are regarded as decomposable;

step 6. decomposing the mobile diagnosis and treatment tasks with the resource descriptors and the intelligent health tasks with the resource descriptors that are decomposable according to the WBS decomposition structure, so as to obtain the mobile diagnosis and treatment tasks with the resource descriptors and the intelligent health tasks with the resource descriptors that have the smallest granularity;

step 7. processing the mobile diagnosis and treatment tasks and the intelligent health tasks processed by the task decomposition unit respectively and accordingly with the optimal resources, thereby obtaining the process results of the intelligent health tasks; and making dynamic evaluations during the processing of the mobile diagnosis and treatment tasks, thereby obtaining the process results of the mobile diagnosis and treatment tasks;

step 8. judging the process results of the intelligent health tasks and the mobile diagnosis and treatment tasks, if the process results are successful, releasing the matched optimal resources; otherwise, returning to the step 4 to rematch resources, thereby improving the efficiency and performance of task scheduling process in the mobile health environment, and utilizing the network resources better to serve the mobile health tasks.

What is claimed is:

1. A task scheduling method for mobile health, comprising the following steps:

step 1: describing and classifying health tasks with a Resource Description and Access (RDA)framework, and obtaining mobile diagnosis and treatment tasks and intelligent health tasks;

step 2: measuring the mobile diagnosis and treatment tasks and the intelligent health tasks, obtaining corresponding resource descriptors, packaging the mobile diagnosis and treatment tasks and the intelligent health tasks respectively and obtaining the mobile diagnosis and treatment tasks with the resource descriptors and the intelligent health tasks with the resource descriptors;

step 3: identifying task priorities for the mobile diagnosis and treatment tasks with the resource descriptors and the intelligent health tasks with the resource descriptors respectively with a secondary scheduling method and obtaining a resource schedule table;

step 4: matching corresponding optimal resources for the mobile diagnosis and treatment tasks with the resource descriptors and the intelligent health tasks with the resource descriptors with annealing algorithm;

step 5: matching the mobile diagnosis and treatment tasks with the resource descriptors and the intelligent health tasks with the resource descriptors with a Work Breakdown Structure (WBS) decomposition structure, if matching successfully, the received mobile diagnosis and treatment tasks with the resource descriptors and the intelligent health tasks with the resource descriptors are indecomposable, otherwise they are regarded as decomposable;

step 6: decomposing the decomposable mobile diagnosis and treatment tasks with the resource descriptors and the decomposable intelligent health tasks with the resource descriptors according to the Work Breakdown Structure (WBS), and obtaining the mobile diagnosis and treatment tasks with the resource descriptors and the intelligent health tasks with the resource descriptors of a smallest granularity;

step 7: processing the mobile diagnosis and treatment tasks and the intelligent health tasks processed in step 6 respectively and accordingly with the optimal resources, thereby obtaining process results of the intelligent health tasks; and dynamically evaluating during processing of the mobile diagnosis and treatment tasks, thereby obtaining process results of the mobile diagnosis and treatment tasks; and step 8: judging the process results of the intelligent health tasks and the mobile diagnosis and treatment tasks, if the process results are successful, releasing matched optimal resources; otherwise, returning to the step 4.

* * * * *